United States Patent [19]

Peterson

[11] Patent Number: 4,814,280
[45] Date of Patent: Mar. 21, 1989

[54] PLASMA AND HEMOGLOBIN-ASSOCIATED ACETALDEHYDE AS A MARKER OF ALCOHOL USE

[76] Inventor: Charles M. Peterson, 1075 San Antonio Creed Rd., Santa Barbara, Calif. 93111

[21] Appl. No.: 82,518

[22] Filed: Aug. 7, 1987

[51] Int. Cl.$^4$ ............................................. G01N 33/48
[52] U.S. Cl. .................................... 436/128; 436/132; 436/161; 436/172
[58] Field of Search ............... 436/128, 130, 132, 113, 436/161, 172, 175, 178

[56] References Cited

PUBLICATIONS

Stevens et al., Acetaldehyde Adducts with Hemoglobin, J. Clin. Invest. vol. 67 Feb. 81, pp. 361–369.
Homaidan et al., Acetaldehyde Hemoglobin Adducts: An Unreliable Marker of Alcohol Abuse, Clin. Chem. 30/3, 480–482 (1984).
Stahovec et al., Trace Analysis of Aldehydes by Precolumn Fluorigenic Labeling with 1,3-Cyclohexanedione and Reversed-Phase H.P.L.C., J. of Chromatography 298 (1984) 399–406.

Primary Examiner—Barry S. Richman
Assistant Examiner—Lyle Alfandary-Alexander
Attorney, Agent, or Firm—Marvin E. Jacobs

[57] ABSTRACT

An improved fluorigenic, high-performance, liquid chromatography (HPLC) assay comprises reacting plasma and hemolysate samples with cyclohexanedione in the presence of ammonium ion to form a methylacridine dione fluorigenic species that is stable and exhibits high recovery values. Acetaldehyde content was determined by comparing the fluorescent peaks of the HPLC eluted band with standard peaks. Alcohol intake by the subject was detected by comparing the acetaldehyde levels to those of teetotalers.

15 Claims, 1 Drawing Sheet

PLASMA AND HEMOGLOBIN-ASSOCIATED ACETALDEHYDE AS A MARKER OF ALCOHOL USE

DESCRIPTION

Technical Field

The present invention relates to an assay for the determination of alcohol ingestion and, more particularly, this invention relates to the very sensitive assay for determination of plasma acetaldehyde and hemoglobin-associated aldehydes by formation, separation and detection of a fluorescent adduct of acetaldehyde.

Background of the Invention

A significant portion of the population of industrialized countries has a dependency or addiction to alcohol. It is estimated that in the United States, there are at least 10 million persons with an alcohol dependency. In many other countries alcohol abuse has reached epidemic proportion. Research has determined that alcohol dependency can be reversed or cured with long-term treatment programs involving counselling and behavior modification. Outpatient programs allow the patient to live and work under normal conditions. Even after a patient is discharged from a short-term treatment program, the patient is requested to return for periodic check up visits which can be a few weeks to a few months apart.

Alcohol is metabolized by the body fairly quickly, usually within 1 to 4 hours. Since the patient visits the clinic periodically, he could be ingesting alcohol between visits and conventional breath, wine or blood analysis for alcohol would not reveal alcohol ingestion and the therapist would not be aware of the subject's return to alcohol use if the subject lies to the therapist. It has not been determined whether alcohol dependency or addiction is based on a chemical dependency in the body or a psychological dependency or both. In any case, it is quite easy for a patient under treatment or a patient who has been off alcohol for an extended period, to become re-addicted on consumption of alcohol in one or more episodes. This tendency to lapse back in alcohol dependency is higher for outpatients who are subjected to the stresses encountered in their personal and professional lives.

| List of Cited References | |
|---|---|
| U.S. PAT. NO. | PATENTEE |
| 2,827,364 | Ladisch |
| 3,563,708 | Stone et al |
| 3,645,696 | Iannacone et al |
| 3,649,199 | Littlejohn |
| 3,690,838 | Luckey |
| 3,888,628 | Graham |
| 4,169,676 | Kaiser |
| 4,181,853 | Abu-Shumays et al |
| 4,419,452 | Imai et al |
| 4,471,055 | Opp |
| 4,556,635 | Hitzman et al |
| 4,590,166 | Ellin et al |
| 4,617,278 | Reed |
| 4,626,355 | Joustra et al |

Literature References

1. Lieber CS, Baranona E, Matsuda Y, Salaspuro M, Hasumura Y., Matsuzaki S: Hepatotoxicity of acetaldehyde. Adv Exp Med Biol 126:397–411, 1980.

2. Lindros KO: Human blood acetaldehyde levels with improved methods, a clearer picture emerges. Alcohol Clin Exp Res 7:70–75, 1983.

3. Eriksson CJ: Problems and pitfalls in acetaldehyde determinations. Alcohol Clin Exp Res 4:22–29, 1980.

4. Stevens VJ, Fantl, WJ, Newman CB, et al.: Acetaldehyde Adducts with Hemoglobin, J Clin Inves, 67:361–369, 1981.

5. Peterson CM, Nguyen LB: "Clinical Implications of Acetaldehyde Adducts with Hemoglobin," in Aldehyde Adducts in Alcoholism, (ed) Michael A. Collins, Alan R. Liss, Inc., N.Y., 1985 pp. 18–30.

6. Homaidan FR, Kricka LJ, Clark PMS, et al: Acetaldehyde-hemoglobin adducts: an unreliable marker of alcohol abuse. Clin Chem 30:480–482, 1984.

7. Peterson CM, Polizzi CM, Frawley PJ: Artefactual increase in hemoglobins Ala-b in blood from alcoholic subjects. Alcohol Clin Esp Res 10:219–220, 1986.

8. Gordis E, Herschkopf S: Application of isoelectric focusing in immobilized pH gradients to the study of acetaldehyde-modified hemoglobin. Alcohol Clin Exp Res 10:311–319, 1986.

9. Stahovec WL, Mopper K: Trace analysis of aldehydes by pre-column fluorigenic labeling with 1, 3-cyclohexanedione and reversed-phase high-performance liquid chromatography. J Chromatography 298:399–406, 1984.

10. Di Padova C, Alderman J, Lieber: Improved methods for the measurement of acetaldehyde concentrations in plasma red blood cells. Alcoholism Clin and Exp Research 10:86–89, 1986.

11. Israel Y, Hurwik E, Niemela O, Arnon R. Monoclonal acetaldehyhde containing epitopes in acetaldehyde-protein adducts. Prin. Nat'l Acad. Sci. USA 83:7923–7927, 1986.

Statement of the Prior Art

However, there are alcohol metabolites such as acetaldehyde that remain in the system for long periods after alcohol ingestion. There is a background level of acetaldehyde that is present in the blood of all humans. However, the background level for teetotalers is significantly different than the level of acetaldehyde for alcohol users.

The measurement of acetaldehyde has been a source of concern and debate due to the potential clinical importance of this primary metabolite of alcohol and to difficulties related to its assay in biological samples (1–3). Two main difficulties exist concerning the measurement of acetaldehyde in plasma and whole blood: the first is related to its disappearance from blood prior to measurement, and the second is related to the formation of acetaldehyde in blood after its collection (3).

The observation that acetaldehyde partitions rapidly into the erythrocyte and forms relatively stable adducts with hemoglobin helped explain some of the above problems and gave rise to the hope that the measurement of these adducts might provide a marker for alcohol intake (4,5). However, measurements of acetaldehyde hemoglobin adducts based on changes in pI (isoelectric) induced by adduct formation have proven unreliable due in part to the small amounts of acetaldehyde involved and in part to an artifactual increase in fast eluting hemoglobins on cation exchange chromatography which occurs during storage of blood from alcoholic subjects (6–8).

A radioactive assay for hemoglobin associated aldehyde is very complex requiring borohydride reduction during the formation of an epitope and binding the epitope to a monoclonal antibody specific for the epitope. This assay also results in non-specific binding leading to anomalous results.

Di Padova[10] describes a fluorigenic assay for the determination of acetaldehyde in plasma and whole blood. The absolute values found in samples of plasma were lower than those measured by the standard semicarbazide-plasma procedure. The preparation of the fluorimetric species was complex, the run time was excessive (about 25 minutes) and the sensitivity (0.4 $\mu$M) is less than acceptable for a clinical testing program.

Stahovec[9] discloses analysis of diverse aldehydes by reaction of the aldehyde with 1, 3 cyclohexanedione to form a fluorigenic species followed by reversed-phase high-performance liquid chromotography (HPLC). Stahovec simply discloses a general analytical technique. The technique would not be applicable to plasma without separatio of erythrocytes and there is no indication or recognition of determination of plasma acetaldehyde as a marker for alcohol ingestion in humans.

The patent literature describes other procedures for determining alcohol content of blood or other fluids or for the fluorimetric assay of aldehyde or of protein materials.

Ladisch discloses quinone reaction with protein (an amine) to form a fluorescent species. Opp determines aldehyde colorimetrically by reaction with a triazone or a cyclohexanedione. Imai et al, Abu-Shumays and Ellin et al disclose fluorescence detection of an LC liquid in a flow cell.

Stone et al enhances fluorescence of a carbalkoxyhydroxy-quinoline by extracting the animal feed or tissue sample with alcoholic solution of an alkaline earth metal.

The remaining patents disclose alcohol assay by diverse methods. Luckey discloses a GC blood analyzer. Graham adsorbs blood on a porous support before adding a colorimetric agent. Littlejohn discloses analysis of drug metabolites by GC. Kaiser uses IR laser absorption to determine blood metabolites. Reed relates to a colorimetric kit for determination of alcohol in gasohol. Joustra determines alcohol consumption by analysis for isotransferrins. Iannocone dries hydrazine on a support as a colorimetric-reagent for determining aldehyde in crankcase oil as an indicator of the presence of ethylene glycol. Hitzman measures dissolved oxygen by means of an alcohol oxidase electrode to detect presence of alcohol in water.

STATEMENT OF THE INVENTION

An improved fluorigenic, high-performance, liquid chromatography assay is provided by the present invention that has the specificity, accuracy, sensitivity and precision to be of clinical utility. The fluorgenic species is prepared by adding a cyclohexanedione to the blood sample in the presence of ammonium ion to form a methylacridine-dione. The reaction of 1, 3-cyclohexanedione (CHD) with acetaldehyde in water in the presence of ammonium and acetaldehyde is illustrated below:

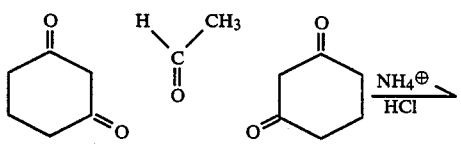

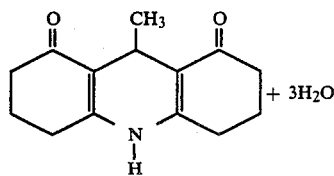

Two molecules of 1,3-cyclohexanedione (CHD) react with ammonium and acetaldehyde in the presence of HCl to form 1, 2, 3, 4, 5, 6, 7, 8, 9, 10-decahydro-9-methylacridine-1,8-dione and water.

The fluorigenic species is simple to prepare and the run time per sample is very short, on the order of 5–6 minutes. The fluorigenic species is stable in the prepared plasma or hemolysate samples showing a retention time identical to the reference standard and exhibiting very high recovery values. The major advantage of the assay of the invention is the specificity and sensitivity in the picomole range. The intra-assay precision is less than 3.5% and inter-assay precision is less than 15%. The high sensitivity and precision demonstrates that there is a significant difference in acetaldehyde levels between teetotalers and individuals who consume alcohol. The acetaldehyde assay of the invention can be used as a marker for the identification of alcohol abuse and/or acoholism.

These and many other advantages and attendant features of the invention will become apparent as the invention becomes better understood by reference to the following detailed description when considered in conjunction wth the accompanying drawings.

DESCRIPTION OF THE INVENTION

Figure 2:
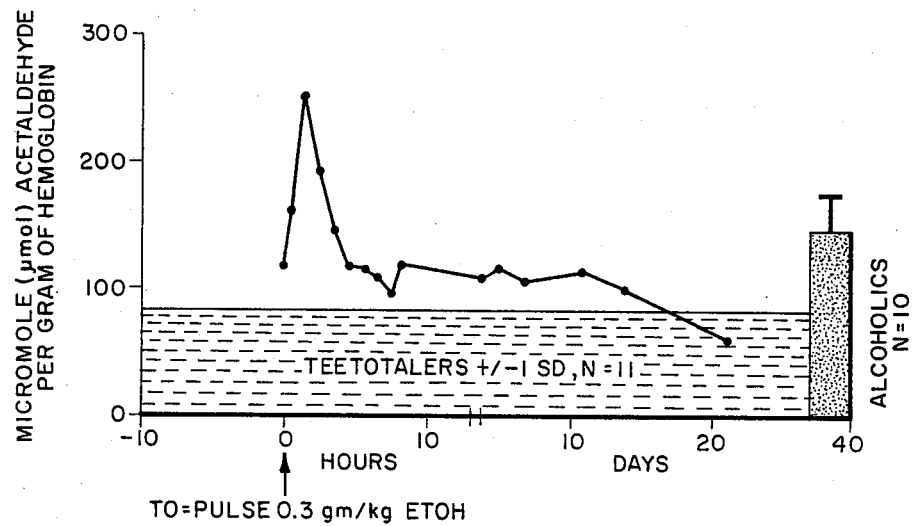
FIG. 2 is a graph showing the acetaldehyde concentration in a group of subjects over a twenty-two day period.

The source of the ammonium ion can be any salt of ammonium whether organic or inorganic. A preferred source is a salt of a weak acid such as ammonium acetate. The ammonium ion is present in excess usually from 10 to 40 percent by weight. A strong acid such as HCl may be present to promote the cyclization of the dione to acridine. The acid is typically present in an amount from about 5 to 20 percent by volume.

The reagent is purified by heating in a sealed container at a temperature from about 40° C. to 75° C. for at least one-half hour. After cooling, the reagent is passed through filters and solid adsorption media to remove impurities. The reagent was then calibrated.

Anticoagulent was added to the blood samples before centrifuging and separation of plasma and erythrocytes. The erythrocytes were treated to form hemolysate incubated in saline for at least 4 hours, suitably overnight, at a temperature below 10° C. to remove the labile adduct of acetaldehyde from hemoglobin.

The purified reagent is then reacted with plasma or hemolyste for at least 30 minutes at elevated temperature, generally from 40° C. to 75° C. Hemoglobin concentration was adjusted prior to reaction with the reagent. The plasma sample was prepared for HPLC by adding a hydrocarbon solvent, for example isooctane, to the reaction mixture, centrifuging, removing the aqueous layer and recentrifuging and filtering prior to injection into the HPLC. The hemoglobin samples were prepared for injection by centrifuging and separating the aqueous layer.

Examples of Practice follow:

EXAMPLE 1

Preparation of Reagent

All solvents and reagents were of HPLC or analytical grade. 400 mg 1,3-cyclohexanediaone (CHD, Fluka Chemicals, Buchs, Switzerland), 10 g $NH_4COOCH_3$ and 3.2 ml concentrated HCl were mixed in 30 ml $H_2O$. To remove contaminants, the reagent was heated in a sealed bottle at 60° C. for 1 hour. The reagent was cooled and passed sequentially through a C-18 Sep-Pak cartridge (Waters Associates, Milford, Mass.).

EXAMPLE 2

Calibration of Reagent

To calibrate the reagent with acetaldehyde, 1 ml of purified reagent was added to 1 ml of varying concentrations of acetaldehyde (0, 0.25, 0.5, 1.0, 2.5, 5.0 $\mu M$), placed in a sealed glass scintillation vial and reacted for one hour at 60° C. The reaction was stopped by placing the sample in an ice bath, and 20 $\mu l$ of each sample was injected onto an HPLC system (Beckman Instruments, Anaheim, Calif.) equipped with a C-18 guard column and with a 250 mm C-18 column (Ultrasphere ODS) developed with 70:30 (v/v) $H_2O$/Acetonitrile at ml/min. Peaks were detected by measuring fluorescence with a 305-395 nm excitation filter and a 450 ±3.5 nm emission filter. Peak integrations were performed on a Spectra-Physics 4270 integrator.

EXAMPLE 3

Sample Preparation

One ml of CHD reagent was reacted with 1 ml plasma or hemolysate for 1 hour at 60° C. for determination of acetaldehyde levels in plasma or acetaldehyde associated with hemoglobin. Hemoglobin concentration was adjusted to 25 mg/ml prior to reaction with CHD as determined by measurement of absorbance at 540 nm. Plasma protein concentrations were measured by the biuret procedure (Sigma Diagnostics, St. Louis, Mo.). Plasma samples were prepared for injection by adding isooctane to the reaction mixture, vortexing and centrifuging (20,000×g) for 15 min at 4° C. The aqueous layer was carefully removed and spun at 20,000×g for 20 min at 4° C. The aqueous layer was filtered prior to injection. Hemoglobin samples were prepared for injection by spinning the reaction mixture in a microfuge (Beckman, Anaheim, Calif.) for 4 min. The aqueous supernatant was injected directly. Results are expressed as uM acetaldehyde as determined from the standard curve of acetaldehyde concentrations. Nanomoles acetaldehyde per gram protein was calculated by dividing the acetaldehyde concentration by the protein concentration. Statistical analysis utilized the Student's T Test for unpaired samples.

Clinical Test

Teetotalers were recruited from the community and were defined for the purposes of the study as someone who had not consumed alcohol for three months or longer. Alcoholic subjects were recruited on admission to an alcohol treatment program. Blood was drawn into vacuum tubes containing ethylenediaminetetraacetic acid as an anticoagulant and placed on ice in the refrigerator. Samples were then centrifuged at 4° C. (1600 g×10 min) and plasma and erythrocytes were separated. The erythrocytes were washed×3 in normal saline and were incubated in saline overnight at 4° C. to remove the labile adduct of acetaldehyde from hemoglobin (4). The red cells were hemolyzed with 1.5 times their volume of distilled water and 0.4 times their volume of $CCl_4$ for 15 min at room temperature with occasional stirring. Stroma were removed by centrifuging×2 at 20,000 g for 20 min at 4° C. (4). Both plasma and hemoglobin samples were stored at −80° C. until assayed.

Figure 1:
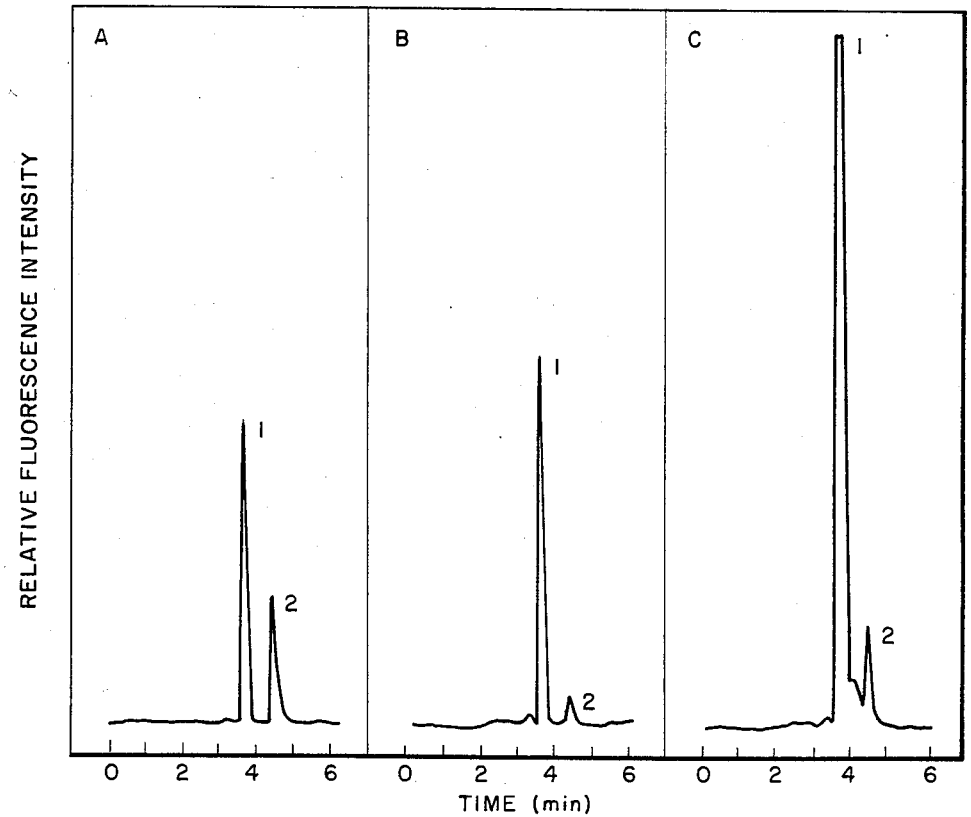
FIG. 1 shows HPLC chromatograms of (A) acetaldehyde standard (2.5 $\mu$M), and (B) plasma, and (C) hemoglobin from a teetotaler following reaction with CHD reagent. Peak 1 represents formaldehyde and peak 2 represents acetaldehyde.

FIG. 1 shows representative chromatograms obtained from an acetaldehyde standard (A), plasma (B), and hemolysate (C). In both biological samples, the peaks of acetaldehyde (1) were clear with minimal tailing and were easily separated from the formaldehyde peak (2). No endogenous plasma or hemoglobin-associated component interfered with the separation. The acetaldehyde peaks in biological samples exhibited a retention time identical with that obtained from the direct injection of the authentic reference standards and a run could be performed in less than 6 min. The calibration plots of peak areas versus concentrations were linear in the range of 0 to 200 pmol acetaldehyde injected. Comparing the slopes of the calibration of standard versus the calibration of biological samples, a mean recovery value of 85% from plasma and 95% from hemoglobin was calculated. The limit of sensitivity of the assay was found to be 2 pmol. The within day CV of the assay was <15% (data not shown).

Table 1 summarizes the data from teetotalers and persons reporting for alcohol treatment.

TABLE 1

| Teetotalers | $\mu M$ | Protein | Alcoholics | $\mu M$ | Protein |
|---|---|---|---|---|---|
| PLASMA ACETALDEHYDE | | | | | |
| 1. | 0.47 | 5.7 | 1 | 0.95 | 13.7 |
| 2. | 0.45 | 5.1 | 2 | 0.66 | 8.5 |
| 3. | 0.46 | 4.6 | 3 | 0.72 | 9.2 |
| 4. | 0.46 | 5.5 | | | |
| 5. | 0.46 | 5.1 | 4 | 1.29 | 17.4 |
| 6. | 0.37 | 3.9 | 5 | 0.53 | 5.5 |
| 7. | 0.39 | 4.6 | 6 | 0.46 | 5.2 |
| 8. | 0.42 | 4.9 | | | |
| 9. | 0.38 | 4.4 | | | |
| | | | $p = 0.005$ | | |
| Mean ± SD | 0.43 ± 0.04 | 4.87 ± 0.56 | | 0.77 ± 0.31 | 9.92 ± 4.87 |

TABLE 1-continued

| Teetotalers | μM | Protein | Alcoholics | μM | Protein |
|---|---|---|---|---|---|
| | | p = 0.007 | | | |
| HEMOGLOBIN ASSOCIATED ACETALDEHYDE | | | | | |
| 1. | 1.53 | 63.5 | 1. | 4.15 | 167.0 |
| 2. | 2.26 | 93.0 | 2. | 2.24 | 94.5 |
| 3. | 2.07 | 86.3 | 3. | 2.27 | 89.7 |
| 4. | 1.44 | 55.8 | 4. | 10.70 | 431.0 |
| 5. | 2.37 | 98.3 | 5. | 1.71 | 71.2 |
| 6. | 2.10 | 84.7 | 6. | 2.77 | 117.0 |
| 7. | 1.56 | 65.0 | 7. | 1.79 | 78.2 |
| 8. | 1.45 | 59.2 | 8. | 5.14 | 223.0 |
| 9. | 2.11 | 89.4 | 9. | 4.31 | 180.0 |
| 10. | 1.54 | 63.1 | 10. | 2.40 | 100.0 |
| 11. | 1.39 | 57.7 | | | |
| | | p = 0.029 | | | |
| Mean ± SD | 1.80 ± 0.38 | 74.2 ± 16.1 | | 3.75 ± 2.72 | 155.2 ± 109.0 |
| | | p = 0.025 | | | |

As can be seen, there are significant differences between the teetotaler and alcoholic groups in both plasma and hemoglobin-associated acetaldehyde levels. Furthermore, the hemoglobin-associated acetaldehyde levels are about 5-10 fold greater than the levels found in plasma.

FIG. 2 summarizes the test of the eleven subjects. The levels for alcoholic patients are shown on the right and the level for teetotalers is in the lower shaded area of FIG. 2.

The time line is broken to indicate a switch from hours to days. The assay gives a retrospective look at alcohol intake for approximately 21 days. The last point was performed in duplicate on days 21 and 22 and both values were in the "teetotaler range" for Hemoglobin Acetaldehyde (AA).

The levels of both plasma acetaldehyde and hemoglobin associated acetaldehyde were significantly higher in patients reporting to a center for alcohol treatment than the levels encountered in teetotalers. More recent experiments have shown that following a pulse of drinking 0.3 gm/kg alcohol, it takes approximately three weeks to return to levels consistent with the teetotaler population. Therefore, this assay is useful as a marker for alcohol) intake.

The fluorigenic high performance liquid chromatographic assay described has the specificity, accuracy, sensitivity, and precision to be of clinical utility. The absolute values found in sample of plasma are in the same range but somewhat lower than those described by Di Padova et al. using another fluorimetric assay which were in turn lower than those measured by the standard semicarbazide-plasma procedure. However, their values were obtained in "normal volunteers" after the peroral administration of 0.3 g/kg alcohol while the subjects tested by the assay of the invention were either avowed teetotalers or were persons who were reporting to a center for treatment. The major advantages of the assay of the invention are the increased sensitivity, the simplicity of preparation of the reagent, and the short run time per sample.

It is noteworthy that the differences between the teetotaler and alcoholic subject samples were statistically greater for the plasma samples than for hemoglobinassociated acetaldehyde (p=0.007 vs. 0.025 when normalized to protein concentration). The reason for this difference is not clear at the present time but may reflect the numerous problems with erythrocyte formation and kinetics to which the alcoholic individual is prone. Since most of the acetaldehyde would be expected to be bound to protein, it seemed reasonable to adjust the values to protein concentration. Whether the 5-10 fold higher levels of acetaldehyde associated with hemoglobin as compared to levels in plasma are a function of the longer lifespan of the hemoglobin molecule (approximately 10 times the lifespan of plasma proteins) remains to be determined.

These results document that the assay of the invention can measure acetaldehyde in biological samples, and that there is a significant difference in levels between teetotalers and alcoholic individuals.

It is to be understood that only preferred embodiments of the invention have been described and that numerous substitutions, modifications and alterations are permissible without departing from the spirit and scope of the invention as defined in the following claims.

I claim:

1. A method of determining the presence of acetaldehyde in whole blood comprising the steps of:
    adding a reagent including cyclohexanedione and ammonium ion to a whole blood sample;
    reacting the acetaldehyde present in the sample with cyclohexanedione and ammonium ion to form a fluorigenic species;
    separating the species from the sample; and
    fluorimetrically determining the amount of acetaldehyde in the sample.

2. A method according to claim 1 further including the step of establishing a base level of acetaldehyde in the plasma and hemoglobin of teetotalers and comparing the acetaldehyde level of the whole blood sample of subjects to provide an indication of alcohol ingestion.

3. A method according to claim 1 further including the step of establishing a chromatogram of a standard acetaldehyde concentration and comparing the chromatogram of the plasma and erythrocyte samples to said standard to determine acetaldehyde concentration.

4. A method according to claim 1 in which separation of the species includes passing the sample through a liquid chromatographic sorbent.

5. A method according to claim 4 further including the step of adding a hydrocarbon solvent to the whole blood sample and reagent, centrifuging, removing the aqueous layer and recentrifuging and filtering before passing the sample through the sorbent.

6. A method according to claim 1 in which the erythrocyte fraction is hemolyzed by incubation in saline at a temperature below 10° C. to effectively remove the labile adduct of acetaldehyde from hemoglobin.

7. A method according to claim 6 in which the hemoglobin concentration of the hemolyzed fraction was adjusted to form a predetermined hemoglobin concentration hemolysate blood sample before reaction with the reagent.

8. A method according to claim 7 in which the hemolysate sample is centrifuged and the aqueous layer separated before determination of acetaldehyde.

9. A method according to claim 1 in which the fluorigenic species is a methylacridine dione.

10. A method according to claim 9 in which the cyclohexanedione is 1, 3-cyclohexanedione and the fluorigenic species is 1, 2, 3, 4, 5, 6, 7, 8, 9, 10-decahydro-9-methylacridine -1, 8-dione.

11. A method according to claim 10 in which the reagent further includes a strong acid in the amount of 5 to 20 percent by volume.

12. A method according to claim 11 in which the strong acid is hyrochoric acid.

13. A method according to claim 11 in which the source of ammonium ion is a salt of a weak acid.

14. A method according to claim 13 in which the salt is ammonium acetate.

15. A method of determining the ingestion of alcohol by a human subject comprising the steps of:

taking a sample of whole blood from a subject;

separating the whole blood into a plasma sample and a hemoglobin-containing erythrocyte sample;

adding a reagent containing a cyclohexanedione and ammonium ion to each sample to form a methylacridine dione fluorescent species by reaction with acetaldehyde;

passing each sample through a liquid chromatographic sorbent consisting essentially of an ion exchange media to isolate a band containing the species;

subjecting the band to excitation radiation and detecting the peak characteristic of the species;

comparing the peaks to a standard to determine acetaldehyde concentration; and comparing the acetaldehyde concentration of the subject to that of a teetotaler to determine alcohol ingestion.

* * * * *